United States Patent [19]
Cancio et al.

[11] Patent Number: 5,254,111
[45] Date of Patent: Oct. 19, 1993

[54] BARRIER CUFF FOR DISPOSABLE ABSORBENT ARTICLES

[75] Inventors: Leopoldo V. Cancio; Pai-Chuan Wu, both of Cincinnati, Ohio; Thomas R. Ryle, Burlington, Ky.; Robert M. Mortellite, Hamilton; J. David Toppen, Loveland, both of Ohio

[73] Assignee: Clopay Plastic Products Company, Inc., Cincinnati, Ohio

[21] Appl. No.: 988,188

[22] Filed: Dec. 9, 1992

Related U.S. Application Data

[63] Continuation-in-part of Ser. No. 821,342, Jan. 13, 1992, Pat. No. 5,202,173, which is a continuation of Ser. No. 478,935, Feb. 12, 1990, abandoned.

[51] Int. Cl.⁵ .................... A61F 13/15; A61F 13/20
[52] U.S. Cl. .................... 604/385.1; 604/366; 604/378; 604/380
[58] Field of Search .............. 604/385.2, 378–381, 604/383, 385.1, 358, 366

[56] References Cited

U.S. PATENT DOCUMENTS

| | | | |
|---|---|---|---|
| 3,484,835 | 12/1969 | Trounstine et al. | 161/130 |
| 4,029,264 | 6/1977 | Reese | 242/1 |
| 4,153,664 | 5/1979 | Sabee | 264/288.8 |
| 4,223,063 | 9/1980 | Sabee | 428/224 |
| 4,376,147 | 3/1983 | Byrne et al. | 428/167 |
| 4,546,029 | 10/1985 | Cancio et al. | 428/141 |
| 4,657,539 | 4/1987 | Hasse | 604/385.2 |
| 4,704,115 | 11/1987 | Buell | 604/385.2 |
| 4,704,116 | 11/1987 | Enloe | 604/385.2 |
| 4,816,025 | 3/1989 | Foreman | 604/385.2 |
| 4,859,519 | 8/1989 | Cabe, Jr. et al. | 428/131 |
| 4,892,528 | 1/1990 | Suzuki et al. | 604/385.2 |
| 4,938,755 | 7/1990 | Foreman | 604/385.2 |
| 5,021,051 | 6/1991 | Hiuke | 604/385.2 |
| 5,026,364 | 6/1991 | Robertson | 604/385.2 |
| 5,080,658 | 1/1992 | Igaue et al. | 604/385.2 |
| 5,085,654 | 2/1992 | Buell | 604/385.2 X |
| 5,087,255 | 2/1992 | Sims | 604/385.2 X |
| 5,158,819 | 10/1992 | Goodman, Jr. et al. | 604/378 X |
| 5,202,173 | 4/1993 | Wu et al. | 428/131 |

Primary Examiner—Randall L. Green
Assistant Examiner—Elizabeth M. Burke
Attorney, Agent, or Firm—Wood, Herron & Evans

[57] ABSTRACT

An improved barrier cuff for disposable absorbent articles such as a diaper is disclosed. A diaper has a liquid-pervious liner, a liquid-impervious backsheet, and an absorbent core disposed between the liner and backsheet, and elastically contractible leg cuffs. The cuff has a proximal edge and a distal edge and is disposed adjacent margins of the disposable diaper and defines a waste containment pocket with the backsheet and liner frontsheet. The cuff being made of an embossed plastic film having a pattern of stretched and unstretched regions. The plastic film provides ultrasoft cloth-like and quiet material for use as a cuff in comparison to known plastic film or laminates. Leakage prevention and comfort to the user are increased because the body exudates are less capable of leaking out of the absorbent article prior to absorption into the core and the wearing comfort is provided by the ultrasoft cuff.

8 Claims, 2 Drawing Sheets

BARRIER CUFF FOR DISPOSABLE ABSORBENT ARTICLES

This application is a continuation-in-part of application Ser. No. 07/821,342, filed Jan. 13, 1992 now U.S. Pat. No. 5,202,173 which is a continuation of Ser. No. 478,935, filed Feb. 12, 1990, now abandoned.

FIELD OF THE INVENTION

The present invention relates to a waste barrier cuff for an absorbent article, and more particularly, to a waste barrier cuff for a disposable diaper, in which the barrier cuff material is a thermoplastic film having improved cloth-like qualities and being ultrasoft and quiet in use.

BACKGROUND OF THE INVENTION

A major function of absorbent articles used in personal hygiene is to absorb and contain bodily fluids or exudates. Absorbent articles are also intended to prevent contamination by soiling or wetting articles such as clothing or bedding. Very often contamination of clothing or other articles occurs when bodily exudates leak from the absorbent article through gaps or openings where the article meets the wearer's waist, leg, or other body part.

It has become a common practice to use disposable diapers with infants and incontinent people. Disposable diapers generally have a rectangular or hour glass shape and comprise an absorbent material sandwiched between a flexible backsheet and often an inner flexible frontsheet. The outer backsheet typically is liquid-impervious to prevent liquid drawn into the absorbent material from striking through the diaper and soiling additional clothing or bedding. On the other hand, the inner frontsheet is water-pervious to permit the voided liquid to pass therethrough into the absorbent material and provide a dry, comfortable garment.

Plastic films are often used in the fabrication of absorbent articles as replacements for woven fabrics. Plastics used in the industry are generated from high-speed production machinery and often include plastic films having an embossed design. U.S. Pat. No. 3,484,835 issued in 1969 discloses a plastic film embossed with a pattern to simulate a woven taffeta design. The simulated taffeta design disclosed in the above-mentioned patent is only an example of many different designs created and employed by film fabricators in their effort to simulate woven fabrics with respect to visual appearances and physical properties which are advantageous from a manufacturing and consumer standpoint. Another one of many such designs embossed on plastic film is disclosed in U.S. Pat. No. 4,376,147 issued in 1983 and directed to an embossed plastic film simulating a matte finish. More recently, U.S. Pat. No. 4,546,029 was issued on a random embossed thermoplastic film simulating a matte or dull finish.

Waste barrier cuffs made of plastic films or film laminates with paper and nonwoven materials are stiff and noisy. Those cuffs are also uncomfortable when the absorbent articles are worn or come into contact with a person's body. Furthermore, the fabrication of absorbent articles including such cuffs and other features has become more expensive.

As evidenced by the above background, production of plastic film for use particularly in absorbent articles has been a continuously improving technology. However, there still exists a demand for a softer, more cloth-like film that eliminates the artificial effects normally associated with plastics when used in an absorbent article. In particular, there is a need for a barrier cuff on an absorbent article or a leg cuff on a disposable diaper which utilizes a more cloth-like film while providing an effective waste or body exudate containment barrier in a more comfortable and quiet manner.

SUMMARY OF THE INVENTION

This invention is directed to an improved waste barrier cuff on an absorbent disposable article. The barrier cuff is made from an ultrasoft cloth-like embossed plastic film which provides properties heretofore unachieved in plastic films used for waste barrier cuffs on disposable absorbent articles.

Improved waste barrier cuffs provide a more comfortable absorbent article, particularly when embodied in a disposable diaper and consisting of a leg cuff worn by an infant or incontinent person. Furthermore, the improved waste barrier cuff constructed of the ultrasoft cloth-like embossed plastic film provides a less noisy absorbent article in use than prior art plastic films or paper materials previously used for barrier cuffs. In achieving these qualities, the improved waste barrier cuff is less expensive to manufacture than known cuffs made from plastic laminates, for instance.

The ultrasoft cloth-like film used for the improved waste barrier cuff of this invention has an embossed pattern and a plurality of postembossed stretched areas along lines that are spaced uniformly across surface areas of both sides of the embossed film. The stretched areas are separated by nonstretched areas and the stretched areas have a thickness less than the unstretched areas of the embossed film. This pattern of stretched-unstretched areas provides a softer and quieter plastic film in comparison to the embossed film in its normal unstretched state.

In its most preferred form, the barrier cuff is an embossed plastic film having a plurality of postembossed stretched areas spaced along lines at essentially uniform intervals completely across the length of the film. These stretched areas are preferably formed by intermeshing corrugated or gear-like rollers. It has been found that new textures may be achieved in overcoming the artificial look of embossed film by the novel technique of stretching embossed film to make them ultrasoft, cloth-like, and quiet. The stretched areas along lines in the film may be continuous or discontinuous across the width or length of the film. The stretched lines may be spaced diagonally, perpendicularly, or parallel to the length of the film, or in crossing patterns to such length. Barrier cuffs having these different stretched patterns may be achieved by providing multiple sets of stretching rollers either in line or in separate lines for diagonal, transverse, or longitudinal stretching. These techniques for making the film for the barrier cuffs are fully disclosed in the above-mentioned application, Ser. No. 07/821,342, now U.S. Pat. No. 5,202,173 which is incorporated herein by reference.

As developed in the background of this invention, waste barrier cuffs made of plastic films or laminates are rather stiff and noisy, even though they provide an effective containment area for the bodily fluids and exudates. In contrast, the barrier cuffs of this invention are ultrasoft, cloth-like, and quiet. They also provide an effective waste barrier containment cuff. Absorbent articles fabricated with the barrier cuffs are very comfortable when in contact with the wearer.

As mentioned above, the barrier cuffs are made of incrementally stretched embossed plastic film. The stretching of the plastic films does not diminish the liquid impervious nature of the plastic film. The most preferred films of this invention to be used for waste barrier cuffs are relatively thin, on the order of about 0.5 to about 2 mils. However, the advantages of this invention may be achieved in thicker films, on the order of about 5 or more mils in thickness. The depths of the emboss in thin films of about 0.5 to about 2 mils is well established in the art and usually ranges from about 1 to about 5 mils. However, in its broader aspects, this invention is not limited to these embossed depths, but rather is directed to the ultrasoft properties for a waste barrier cuff of a disposable absorbent article. Patents mentioned in the background of this invention disclose films having embossed patterns simulating woven taffeta, matte finishes, and random patterns that may be stretched to provide the ultrasoft, cloth-like, quiet nature of a waste barrier cuff of the present invention.

The above features and advantages of the present invention will be better understood in reference to the accompanying figures and detailed description. It should also be understood that the particular thermoplastic sheet materials, absorbent articles, and patterns of stretched and unstretched film of this invention are exemplary only and are not to be regarded as limitations of the invention.

BRIEF DESCRIPTION OF THE DRAWINGS

Reference is now made to the accompanying figures from which the novel features and advantages of the present invention will be apparent.

DETAILED DESCRIPTION OF THE INVENTION

By way of illustrating and providing a more complete appreciation of the present invention and many of the attendant advantages thereof, the following detailed description is given concerning the novel plastic film properties, absorbent articles made therewith, and methods of production and use thereof.

As used herein, the term "disposable absorbent article" refers to articles which absorb and contain body fluids or exudates. More specifically, these articles are placed against or in proximity to the body of the user to absorb and contain various discharges from the body. They are intended to be discarded after a single use.

Figure 1:
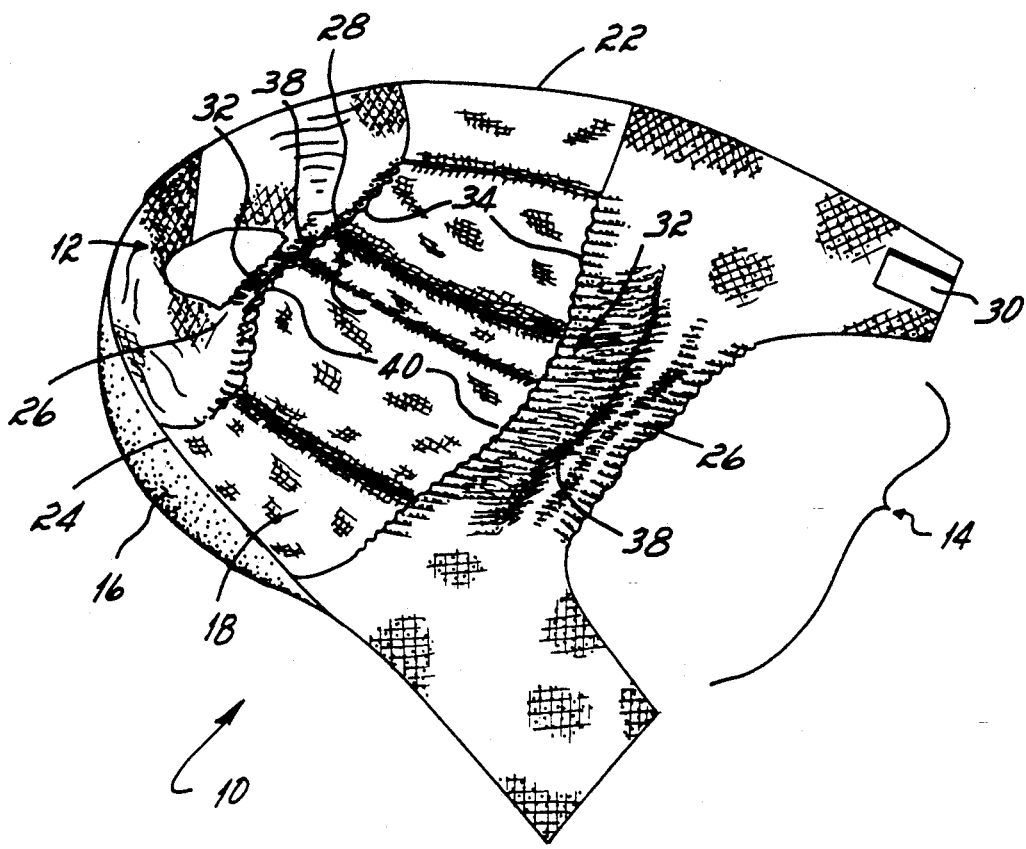
FIG. 1 is a perspective view of a disposable diaper embodiment incorporating the present invention.

A preferred embodiment of the present invention is shown in FIG. 1 as a disposable diaper 10. As used herein, the term "diaper" refers to a garment generally worn by infants and incontinent persons around the lower torso of the user. However, it should be understood that the present invention is also applicable to other disposable articles such as bandages, surgical dressings, surgical drapes, and catamenial pads where the waste barrier cuff serves a useful function to contain waste.

FIG. 1 is a perspective view of a disposable diaper 10 of the present invention having one leg region 12 joined and one leg region 14 in its opened or unattached state. Disposable diapers typically comprise a backsheet 16, a body side frontsheet or liner 18, and an absorbent pad 20 disposed between the backsheet 16 and the liner 18. The absorbent pad 20 can best be seen in the sectional view of the disposable diaper 10 in FIG. 2. The liner 18, although optional in many embodiments of the present invention, is made from a liquid-pervious material. In the preferred embodiment of the present invention, the backsheet 16 is made of a liquid-impervious material. The liner 18 and backsheet 16 are essentially coterminous and form a generally rectangular or hour glass shape with a back waist section 22 and a front waist section 24 and two side sections 26. Intermediate the front waist section 24 and back waist section 22 is a crotch section 28. The disposable diaper 10 is typically placed around a user, such as an infant, and held in place with fastening means 30 such as tape as shown in FIG. 1.

Figure 2:
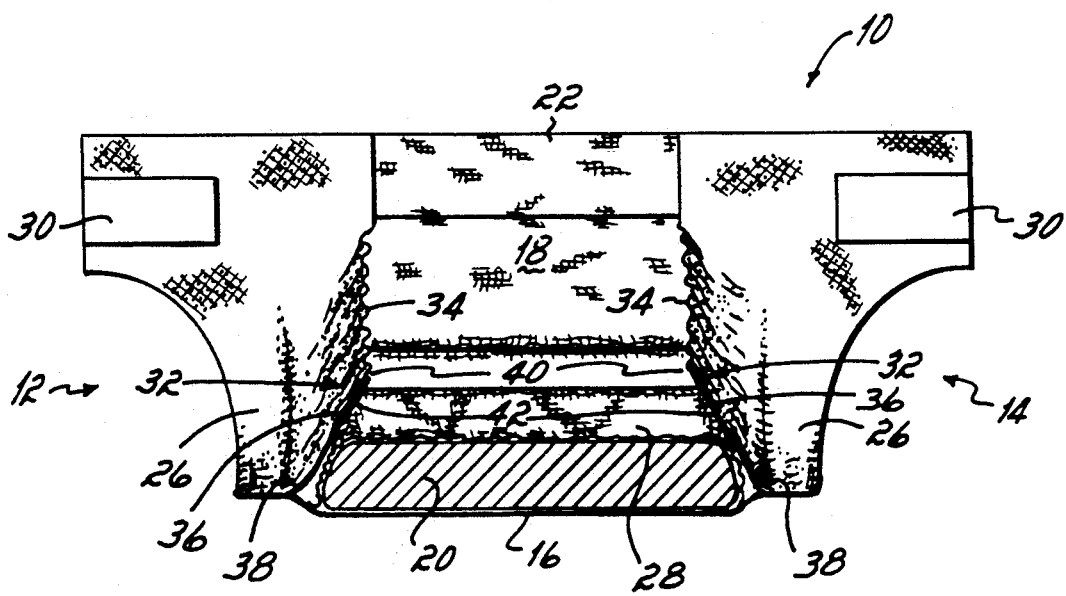
FIG. 2 is a cross-sectional view of a disposable diaper of FIG. 1.

A barrier cuff, or a leg cuff 32 in the preferred embodiment of the disposable diaper 10, is a flexible member which is elastically contractible and disposed adjacent a side of the absorbent article or disposable diaper preferably along each longitudinal side section 26 so that the leg cuff 32 tends to draw and hold the diaper 10 against the leg of the wearer. As used herein, the term "flexible" refers to materials which are compliant and readily conform to the general shape and contours of the body. In addition, the leg cuff 32 comprises elastic members such that the cuff may be contractible so that a distal edge 34 thereof may be sufficiently spaced away from the liner 18 so that a channel 36 is formed to contain and hold bodily fluids and exudates within the absorbent article as shown in FIG. 2.

The distal edge 34 and a proximal edge 38 of the leg cuff 32 are in spaced relation to each other and define the width of the leg cuff 32. The proximal 38 and distal 34 edges may be parallel, nonparallel, rectilinear, or curvilinear in relation to one another. Furthermore, the leg cuff 32 may have a variety of different cross-sectional areas including circular, square, rectangular, or any other geometric configuration. In use, a waste containment pocket 40 is formed along the proximal 38 and distal 36 edges and an inner surface 42 of the leg cuff 32. The containment pocket 40 forms a barrier to the flow of exudates as they tend to move or flow across the liner 18 or waste absorbent pad 20. Thus, the containment pocket 40 holds and contains exudates until the disposable diaper 10 can be removed from the wearer. The containment pocket 40 is further enhanced in the preferred embodiment by using a plastic film material. A plastic film provides a liquid-impervious barrier to the flow of bodily fluids and exudates out from the containment pocket 40.

When the disposable diaper 10 is worn, the leg cuff 32 is typically in contact with the upper thigh portion of the user's leg. While being worn by the user, the leg cuff 32 rubs on this portion of the wearer's body as a result of leg or torso movements. The soft and cloth-like nature of the plastic film used in construction of the leg cuff 32 according to the present invention provides a more comfortable and quieter disposable diaper 10 than the previously available with known plastic films or paper materials.

Figure 3:
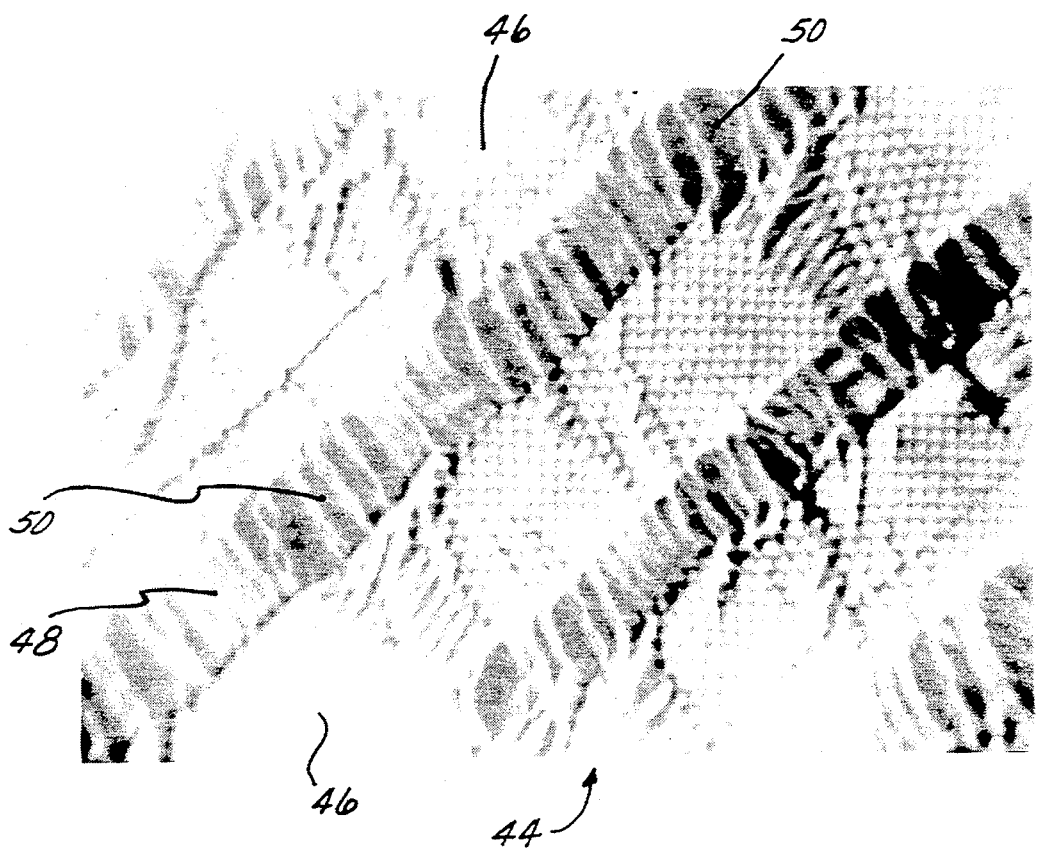
FIG. 3 is a magnified photographic partial view of an ultrasoft embossed film to be used as a waste barrier cuff of the present invention.

A waste barrier cuff or leg cuff 32 according to the present invention is more cloth-like, softer, and quieter than leg cuffs constructed from plastic films or laminates currently used in the industry. FIG. 3 is a magnified photographic partial view of an ultrasoft embossed film 44 suitable for use as the leg cuff 32 in the present invention. The embossed pattern shown in FIG. 3 is disclosed in U.S. Pat. No. 4,376,147 which has been stretched with a plurality of post-embossed stretch areas along two crossing diagonal lines across its width and length. The film shown in FIG. 3 was produced with two passes through diagonal intermeshing stretching rollers. After the first pass, the film was reversed, left to right, for the second pass, creating a pattern of substantially perpendicular stretched lines diagonally oriented relative to the length and width of the film as disclosed in application Ser. No. 07/821,342, and that disclosure is incorporated herein by reference. This method of stretching results in some unstretched areas 46, some areas stretched once 48, and remaining areas stretched twice 50 in a biaxial manner.

FIG. 3 is a photograph of the plastic film 44 at a magnification of about 18× and with the film 44 under slight biaxial tension to remove puckers. The three distinct areas are shown: as the unstretched areas 46, the areas stretched only once 48, and the areas that were stretched twice 50. The areas stretched twice 50 are the thinnest areas of the plastic film 44, with areas being stretched only once 48 being thicker than twice stretched areas 50 and thinner than the unstretched areas 46. The thin areas are stretched preferentially to the thick areas due to lower resistance to the stretching force.

Barrier cuffs made from stretched embossed plastic films of a kind shown in FIG. 3 have a number of advantages; specifically, they are ultrasoft, quiet, and simulate fabric, or cloth in appearance and texture. These cloth-like qualities have been heretofore unachieved in plastic films used for leg cuffs on absorbent disposable articles. These films may be economically processed and advantageously employed in other absorbent articles in addition to disposable diapers such as bandages, surgical dressings, surgical drapes, incontinent articles, and catamenial pads. Leg cuffs and waste barrier cuffs constructed of films of this invention may be provided with woven, nonwoven, and other unique appearances and still have an ultrasoft hand feel and a quiet property, i.e., they make little or no noise when crinkled.

In a preferred form of plastic film used for cuffs of the invention, low to medium density polyethylene, polypropylene, or copolymers thereof are formed into an embossed film by a slot die extrusion means. In achieving the preferred film thickness of between 0.5-2 mils to about 5 mils, along with the necessary embossed depth of about 1 to about 5 mils, conditions are controlled in a manner well within the skill of those knowledgeable in the art of producing embossed plastic films. Thus, process conditions that are obviously controlled to produce embossed film include temperature, pressure exerted between the nip of the embossing roller or system, depth of the engraved design on the steel roll, and the hardness of a rubber roll. Details of such process are disclosed in the above-referenced patents discussed in the background of this invention which are incorporated herein by reference.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. A disposable absorbent article for personal use having a waste barrier cuff comprising:
   a backsheet which forms an article outside layer when used by a person;
   a waste absorbent layer positioned inside of said backsheet; and
   a waste barrier cuff disposed adjacent a margin of the absorbent article defining a waste containment pocket with said backsheet, said cuff being an embossed thermoplastic film having a pattern embossed therein in a normal unstretched state, said film having thick and thin areas and a plurality of post-embossed stretched areas along lines spaced substantially uniformly across a surface area of both sides of said embossed film, said stretched areas being separated by unstretched areas and having a thickness less than said unstretched areas, said thin areas of said embossed film in its normal unstretched state being stretched more readily than said thick areas, said film being ultrasoft and quiet in comparison with said embossed film in its normal unstretched state.

2. The absorbent article of claim 1 further comprising:
   a liquid-pervious liner which forms an article inside layer when the absorbent article is used by the person;
   said absorbent layer positioned between said backsheet and said liner; and
   said cuff disposed adjacent a margin of the absorbent article defining a waste containment pocket with said liner and said backsheet.

3. The absorbent article of claim 1 wherein said thermoplastic film is selected from a group consisting of polyethylene, polypropylene, and copolymers thereof.

4. The absorbent article of claim 1 wherein said thermoplastic film has a thickness on the order of about 0.5 to about 10 mils.

5. The absorbent article of claim 1 wherein said backsheet is liquid-impervious.

6. The absorbent article of claim 1 wherein the absorbent article is selected from the group consisting of a disposable diaper, an incontinent article, a bandage, a surgical dressing, a surgical drape, and a catamenial pad.

7. A disposable diaper having waste barrier leg cuffs comprising:
   a liquid-pervious frontsheet which forms a diaper inside layer when worn by an infant;
   a backsheet which forms a diaper outside layer when worn by the infant;
   an absorbent layer positioned between said backsheet and said frontsheet; and
   a waste barrier leg cuff disposed adjacent opposite margins of the disposable diaper defining a waste containment pocket with said frontsheet and said backsheet, said leg cuff being an embossed thermoplastic film having a pattern embossed therein in a normal unstretched state, said film having thick and thin areas and a plurality of post-embossed stretched areas along lines spaced substantially uniformly across a surface area of both sides said embossed film, said stretched areas being separated by unstretched areas and having a thickness less than said unstretched areas, said thin areas of said embossed film in its normal unstretched state being stretched more readily than said thick areas, said film being ultrasoft and quiet in comparison with said embossed film in its normal unstretched state.

8. The disposable diaper of claim 7 wherein said thermoplastic film has a thickness on the order of about 0.5 to about 2 mils.

* * * * *